United States Patent [19]
Van Dick

[11] Patent Number: 5,562,597
[45] Date of Patent: Oct. 8, 1996

[54] METHOD AND APPARATUS FOR REDUCING PHYSIOLOGICAL STRESS

[76] Inventor: Robert C. Van Dick, 5625 Sugar Creek Ct., Norcross, Ga. 30093

[21] Appl. No.: 509,813

[22] Filed: Aug. 1, 1995

Related U.S. Application Data

[63] Continuation-in-part of Ser. No. 219,088, Mar. 28, 1994, Pat. No. 5,480,374.

[51] Int. Cl.$^6$ .................................................. A61B 17/52
[52] U.S. Cl. ................................ 600/26; 600/9; 600/14
[58] Field of Search .................................. 600/9–15, 26; 607/1, 2

[56] References Cited

U.S. PATENT DOCUMENTS

| | | | |
|---|---|---|---|
| 4,441,498 | 4/1984 | Nordling | 607/32 |
| 4,838,850 | 6/1989 | Rosengart | 600/14 |
| 4,846,178 | 7/1989 | Fuxue et al. | 607/2 |

Primary Examiner—Angela D. Sykes
Assistant Examiner—Stephen Huane
Attorney, Agent, or Firm—Kennedy & Kennedy

[57] ABSTRACT

Physiological stress in a human subject is treated by generating a weak electromagnetic field about a quartz crystal. The crystal is stimulated by applying electrical pulses of pulse widths between 0.1 and 50 microseconds each at a pulse repetition rate of between 0.5K and 10K pulses per second to a conductor positioned adjacent to the quartz crystal thereby generating a weak electromagnetic field. A subject is positioned within the weak electromagnetic field for a period of time sufficient to reduce stress.

17 Claims, 6 Drawing Sheets

METHOD AND APPARATUS FOR REDUCING PHYSIOLOGICAL STRESS

REFERENCE TO RELATED APPLICATION

This is a continuation-in-part of application Ser. No. 08/219,088 filed Mar. 28, 1994, now issued Jan. 2, 1996 U.S. Pat. No. 5,480,374.

TECHNICAL FIELD

The present invention relates to methods and apparatuses for reducing physiological stress in humans. More particularly, the invention relates to methods of reducing physiological stress by increasing an individual's alpha and theta brain waves amplitudes without the need for conscious mental effort or the attachment of devices to the body.

BACKGROUND OF THE INVENTION

The human brain produces electrical brain waves at frequencies ranging from 0 to 64 Hertz (Hz). Within this range are delta waves from 0 to 3 Hz, theta waves from 3 to 8 Hz, alpha waves from 8 to 13 Hz, and beta waves from 13 to 64 Hz. These brain waves are usually present at any given time but in varying magnitudes depending on an individual's thought processes. Beta levels dominate during the alert awakened state. Alpha levels rise and beta levels fall in the light sleep state. Theta levels increase while alpha and beta levels decrease during the deep sleep state. Delta levels rise during a deep-deep sleep state.

It is known that an increase in physiological stress is manifested by low levels of alpha and theta brain waves. An increase in theta frequency levels produce the best physiological stress reduction results, yet they are the most difficult for individuals consciously to produce. While it has been found that an increase in theta frequency levels correspondingly increases alpha frequency levels, the reverse is not true. The more readily increased alpha brain waves do not correspondingly increase theta brain wave levels.

Current techniques used to reduce psychological stress are essentially limited to conscious mental efforts. This is sometimes achievable through pure meditation and sometimes not. Such technique is thus often unreliable. Physiological stress reduction can also be achieved by mental exercises in association with electronic biofeedback instruments that inform individuals of their success or failure in controlling brain wave frequencies, and which assist in altering brain wave frequencies. These bio-feedback instruments typically employ sensors that are attached to the individual's skull and which are electrically coupled with analytic and display apparatuses. Since the individual is physically attached to the instrument, limitations in movement exist which can inhibit the ability of the individual to increase his or her alpha and theta brain wave frequencies and to maintain such increases for a sufficiently period of time to achieve therapeutic results.

Thus, there remains a need for a method of reducing physiological stress that does not require conscious mental effort by individuals and which does not require the attachment of devices to the persons. Accordingly, it is to the provision of such physiological stress that the present invention is primarily directed.

SUMMARY OF THE INVENTION

It has now been discovered that physiological stress reduction can also be achieved with the use of electrical means without the need for conscious effort nor the attachment of devices to persons. By merely exposing a person or persons to a weak electromagnetic field produced in a certain manner, the person's alpha and theta brain wave levels may be increased and thereby reduce physiological stress.

The weak electromagnetic field is produced about a grounded electrode that is coupled with a high voltage pulse generator. The generator transmits pulses of between 5 and 50 microseconds each, at a pulse repetition rate of between 0.5K and 10K pulses per second, to a power electrode, the power electrode and grounded electrode being coupled to a high voltage pulse generator. The subject is positioned within the weak electromagnetic field for a period of time sufficient to cause an increase in alpha and/or theta brain wave levels of the subject.

The method may be practiced with a therapeutic unit that has a treatment space of a size sufficient to accommodate one or more human subjects positioned within the weak electromagnetic field about the grounded electrode. The weak electromagnetic field itself may be specifically prescribed by monitoring brain wave levels of the subject while varying an electrical parameter of the pulse trains generated by the high voltage pulse generator and identifying that parameter which produces a desirable increase in alpha and/or theta brain wave levels for the individual.

In an alternative form of the invention a human subject is treated for physiological stress by stimulating a quartz crystal by applying electrical pulses of pulse widths between 0.1 and 50 microseconds each at a pulse repetition rate of between 0.5K and 10K pulses per second to a conductor positioned adjacent to the quartz crystal thereby generating a weak electromagnetic field about the crystal, and positioning the subject within the weak electromagnetic field. Apparatus for use in this treatment method comprises a quartz crystal, an electrical conductor mounted adjacent the quartz crystal, and means for applying to the conductor electrical pulses of pulse widths of between 0.1 and 50 microseconds each at a pulse repetition rate of between 0.5K and 10K pulses per second.

BRIEF DESCRIPTION OF THE DRAWING

FIG. 3A represents brain wave patterns of a Subject A before utilizing the method of the present invention while

FIG. 4A represents the brain wave patterns of a Subject B before utilizing the method of the present invention while

DETAILED DESCRIPTION OF THE DRAWINGS

Figure 1:
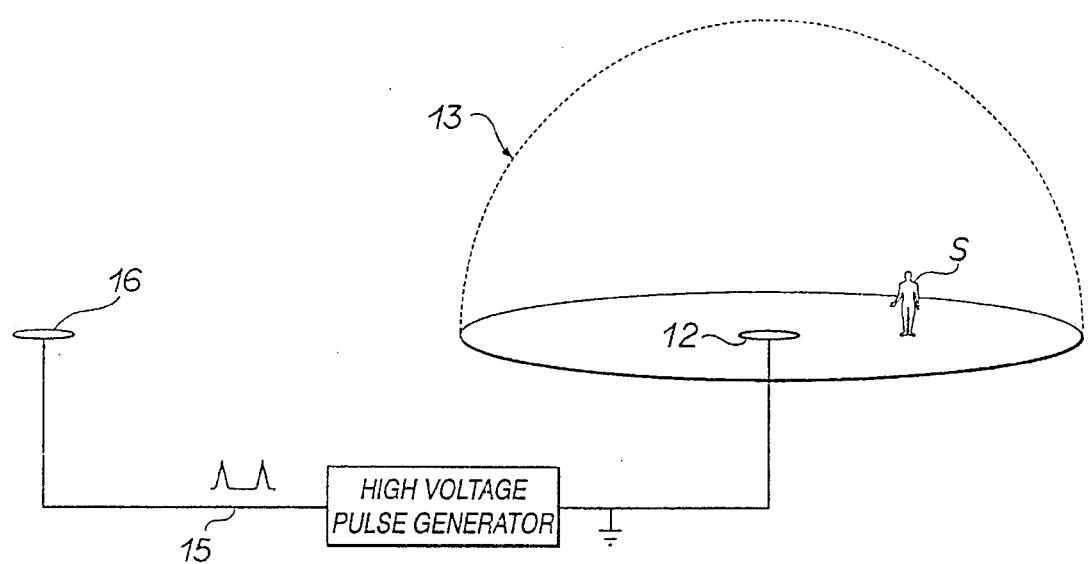
FIG. 1 a schematic diagram of a therapeutic unit that embodies principles of the present invention.

With reference next to the drawing, there is schematically shown in FIG. 1 a therapeutic unit for the treatment of physiological stress in a human subject. The unit has means for generating a weak electromagnetic field about a grounded electrode 12 of generally semi-spherical spatial shape as indicated at 13, there of course being no sharply defined boundary of such. A human subject S is shown positioned within this weak electromagnetic field for treatment which may, for example, be in a room of a building.

The weak electromagnetic field is generated by the use of a high voltage pulse generator that is connected via a well insulated conductor to both the grounded electrode 12 and to earth ground. The generator is also connected via another insulated conductor 15 to a power electrode 16 that is located outside of the weak electromagnetic field.

Figure 2:
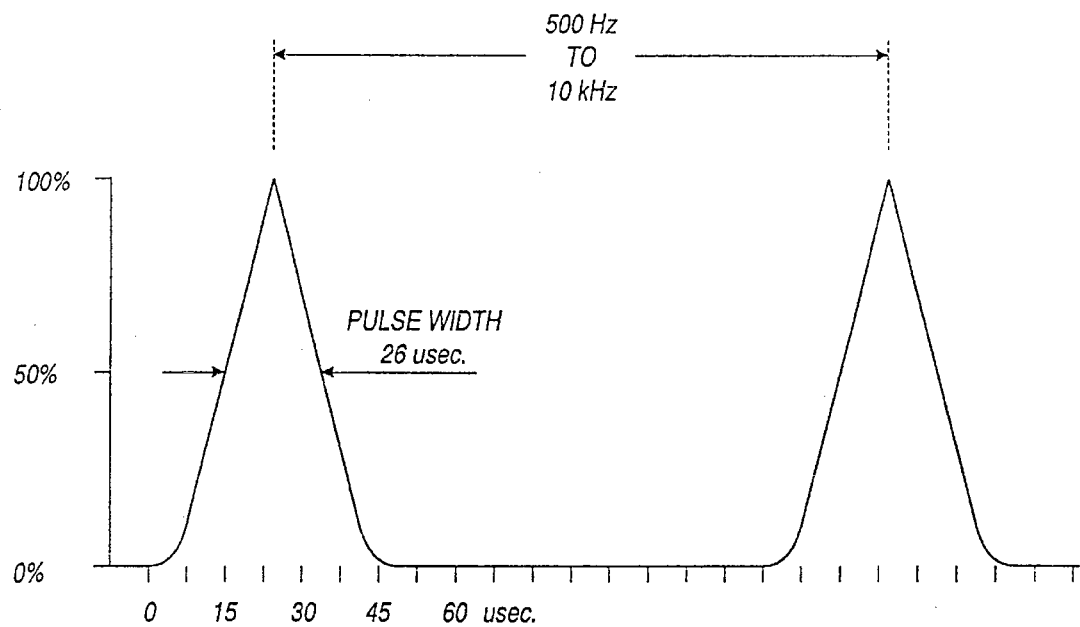
FIG. 2 is a graphic representation of a pulse train generated for use in practicing the method of the present invention.

The high voltage pulse generator is capable of generated pulses of between 0.5KV to 10KV of variable pulse widths and pulse repetition rates. It has been found that pulse widths of between 5 and 50 microseconds as measured at 50% of peak voltage and of a pulse repetition rate of between 500 Hz and 10K Hz, peak to peak, as shown in FIG. 2, produces a weak electromagnetic field that is of substantial therapeutic value here. Moreover, it has been determined that different pulse repetition frequencies or rates within this overall range provide better benefits for different individuals than others. Thus by observing alpha and theta levels in an individual while varying the pulse repetition rate, an optimum or at least a good rate can be determined and prescribed for treatment of that particular individual.

Figure 3A:
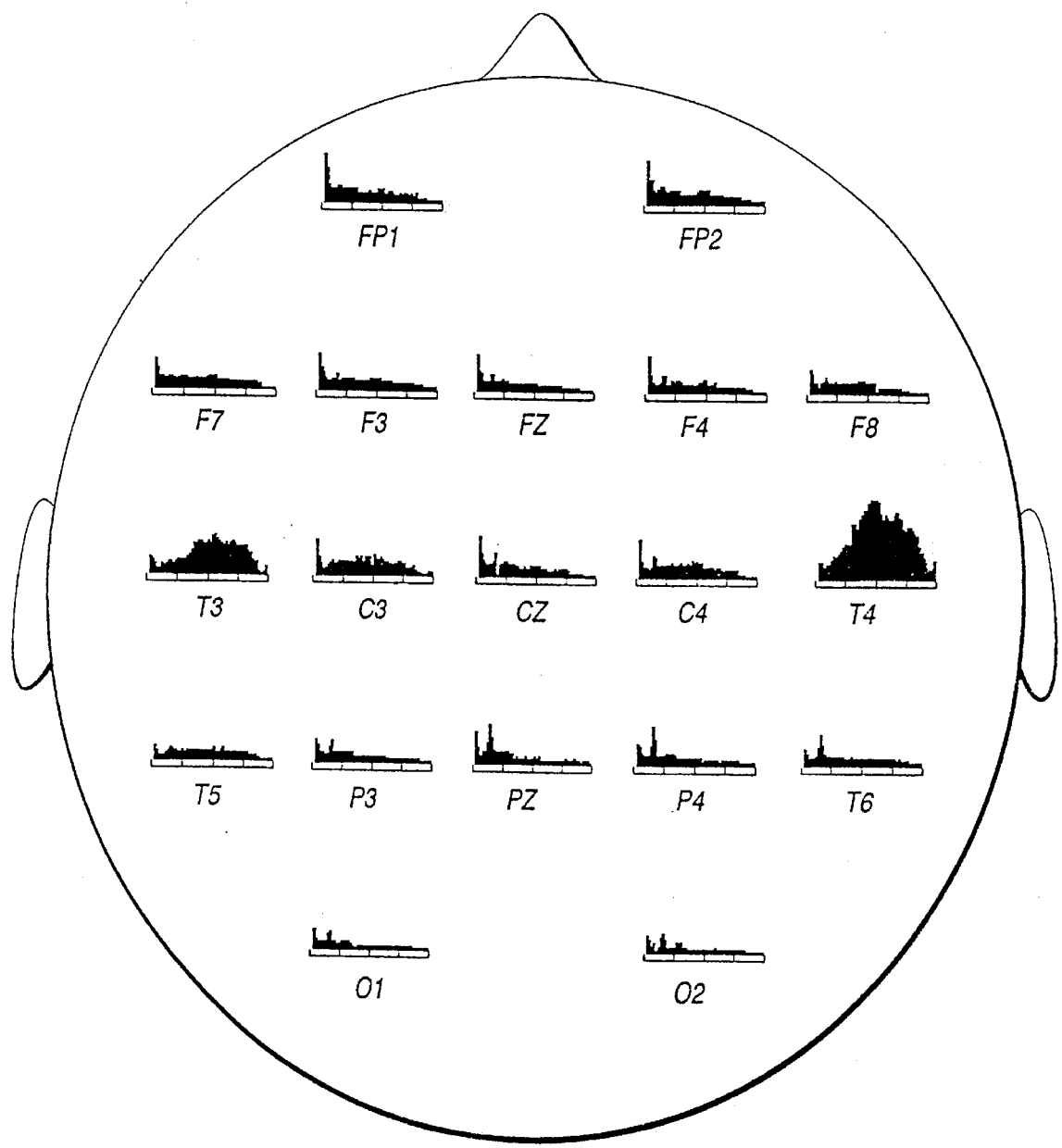
Figure 3B:
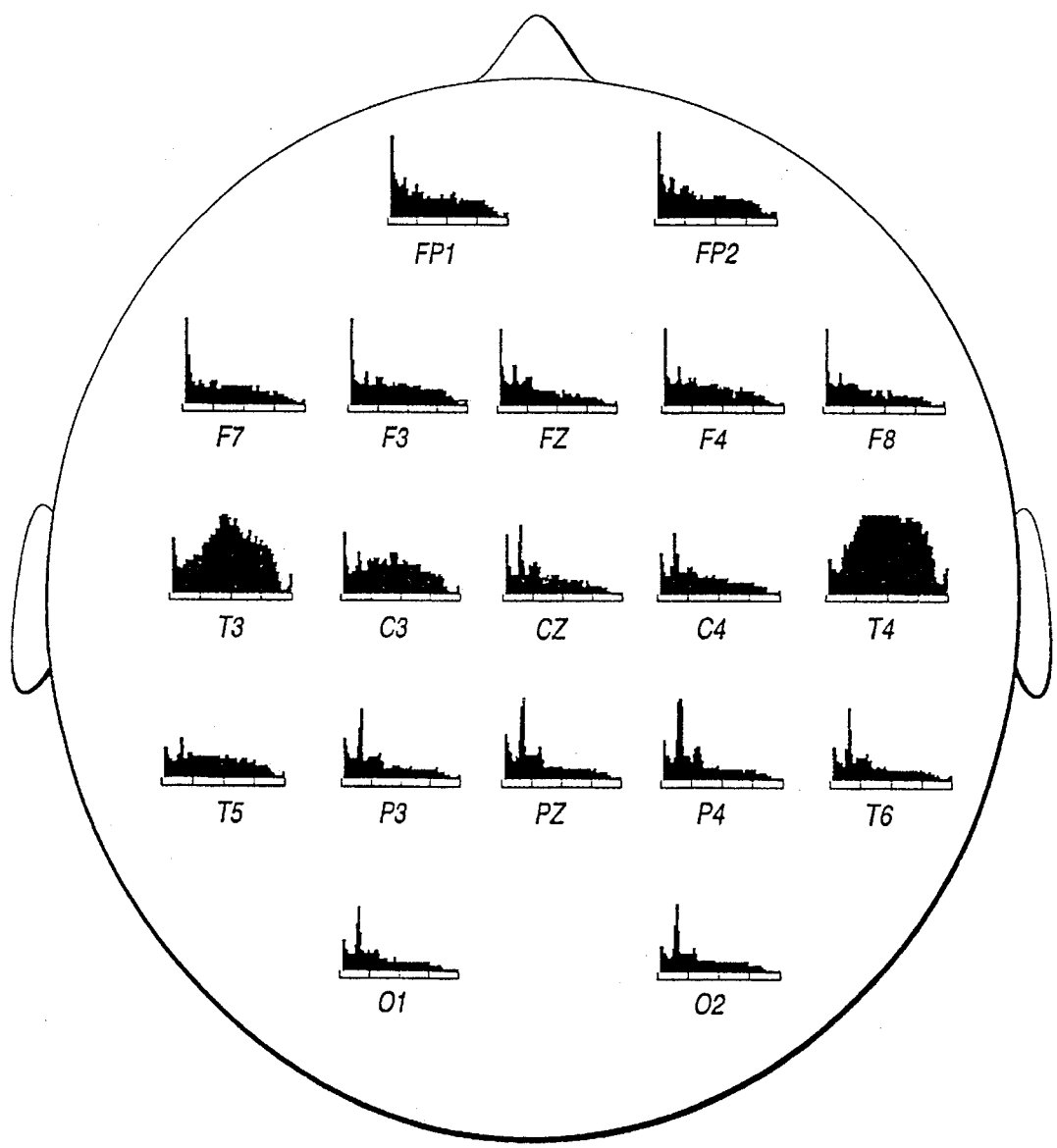
FIG. 3B represents the brain wave patterns of Subject A after utilizing the method of the present invention.
Figure 4A:
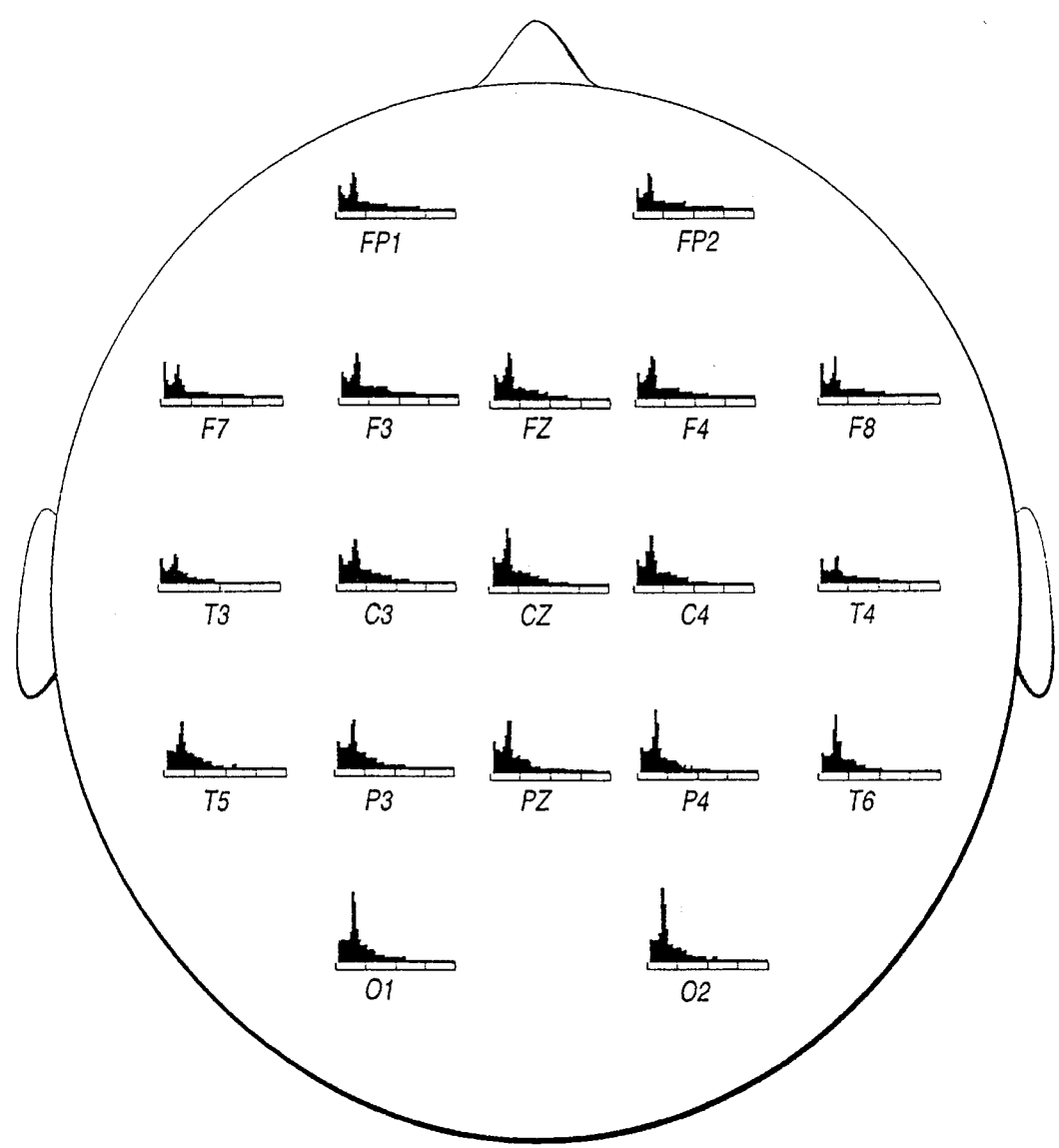
Figure 4B:
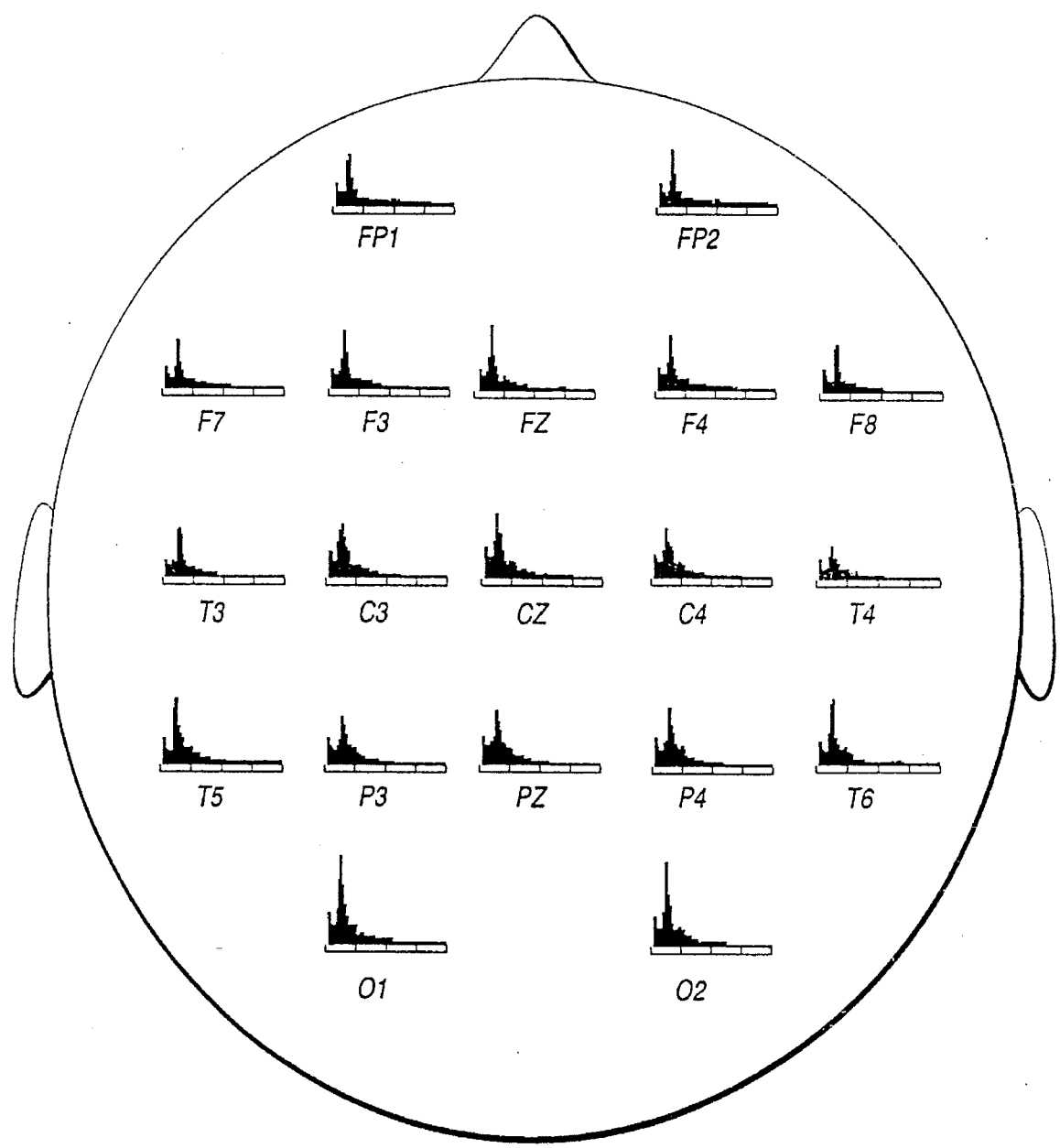
FIG. 4B represents the brain wave patterns of the Subject B after utilizing the method of the present invention.

To determine an at least good or optimum pulse repetition rate for a human subject, electroencephalograms, or EEGs, are taken prior to regular treatments with a specially designed skull cap having electrodes that sense electrical brain waves. This apparatus is conventional and may be purchased from Lexicor, Inc. of Boulder, Colo. or from E. C. I. Electro-Cap International, Inc. of Eaton, Ohio. Before and After treatment electroencephalograms for a first subject are respectively shown in FIGS. 3A and 3B while before and after treatment EEGs for a second subject are respectively shown in FIGS. 4A and 4B. The weak electromagnetic field for the treatment of the first subject was created by pulsing the power electrode with pulses of 26 microseconds each of 1500 volts peak with a pulse rise time of 15 usec from the 10% point to the 90% point of the peak voltage. The pulse repetition rate of the first subject was 2,210, 5,505 and 7,708 pulses per second. A pulse repetition rate of 7,708 was found to achieve the best results. The same parameters were applied to the second subject except that a pulse repetition rate of 7,690 pulses per second was found to be the best.

The subjects were at rest seated in a chair in a room under approximately standard temperature and pressure conditions and illuminated at low levels. The treatment sessions lasted 20 minutes. The benefit derived from the treatment was found to last at least a week.

In FIGS. 3A, 3B, 4A and 4B the designation FPI, FPZ, F7 and so forth represent locations along the skull used in practicing the International 10–20 method of generating EEGs. For example, here F means frontal, T means temporal, O is occipital, P is parietal, C is central and FP is frontal pole and so forth. The horizontal scale below each designation is from 0 to 64Hz, left to right. Thus this scale is large enough to include both alpha and theta frequency wavebands. The irregular black lines or merged black line areas represent sensed levels or amplitudes of brain waves. High spikes in the alpha and theta frequency bands are desired as they cause or are at least associated with physiological stress reduction.

From comparisons of the observed before-treatment and after-treatment alpha and theta wave levels for these two subjects, it can be seen that both achieved an increase in their alpha and theta wave levels when they were treated in accordance with the present method. (Both appear in the first, left-side quarter of the scales.) Each also readily confirmed their feelings of stress reduction. Though such expressions were of course subjective, the detected brain wave patterns readily provided objective verification of such.

The treatment has been proven to be very effective, and repeatable with reliable results. Though a device is attached to a subject for prescribing the best pulse repetition rate for that person, for treatment itself this is not done. During treatment the individual has freedom of dress and posture and may even engage in light mental activities such as reading, eating, listening to music, etc. Treatment sessions need normally last no more than 20 minutes nor more frequently than weekly.

The just described method and apparatus is very effective with the use of a high voltage pulse generator and a grounded electrode. However, there would be advantages to be had if the therapeutic benefits achieved by it could similarly be achieved without the need for a high voltage pulse generator or a grounded electrode, or both. For example, if a conventional consumer battery could be employed, cost and size economy could be achieved. If a grounded electrode were not needed, the apparatus and method could be rendered mobile. It would also be advantageous if the therapy could be applied more continuously rather than in discrete time intervals.

After much experimentation it has been discovered that such is achievable with the use of a quartz crystal that is coupled and stimulated with one or more pulse generators. The quartz crystal stimuli are electrical pulses having pulse widths between 0.1and 50 microseconds each, at a pulse repetition rate of between 0.5K and 10K pulses per second in the pulse train. The pulse voltages may be far below the 500 volts minimum requirement for the earlier described embodiment. The stimulated quartz crystal produces a weak electromagnetic field sufficiently large to encompass the space of a conventional two story house. The weak electromagnetic field can be active continuously, 24 hours a day, so that an individual or individuals may continuously receive stress reduction benefits.

Figure 5:
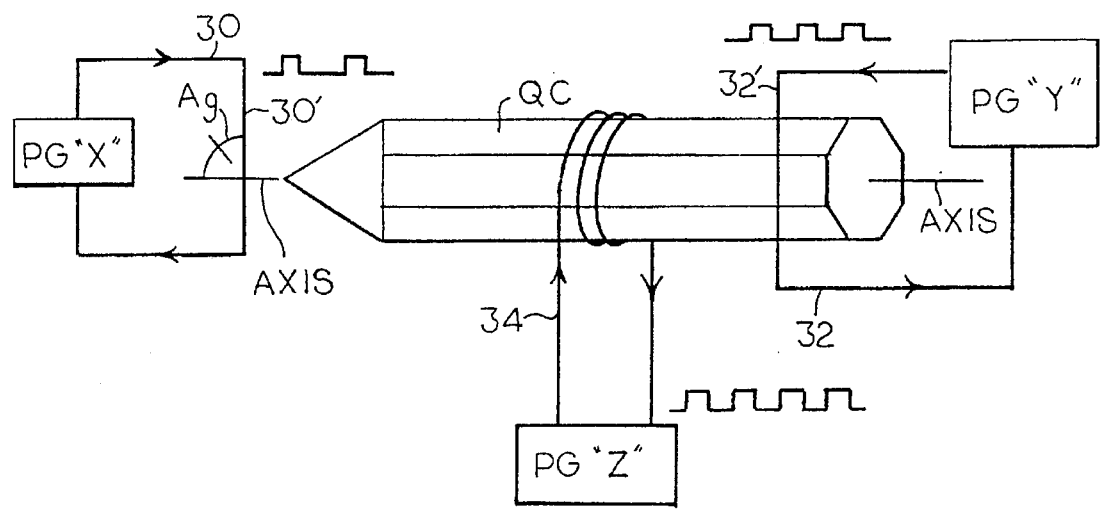
FIG. 5 is a schematic diagram of a therapeutic unit that embodies principles of the invention in another form.
Figure 6:
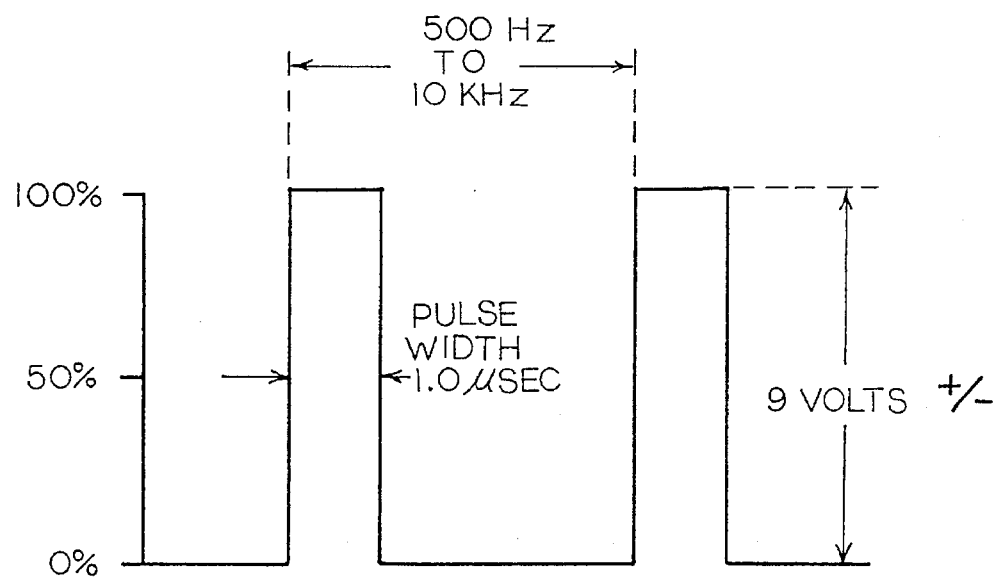
FIG. 6 is a graphic representation of a pulse train generated for use in practicing the method of the invention with the unit shown in FIG. 5.

A low voltage embodiment is illustrated in FIGS. 5 and 6. Here a quartz crystal QC is shown coupled to three 9-volt low voltage pulse generators (PG) x, y and z. An insulated electrical conductor 30 connected across generator x has a linear length 30' (thirty prime) that is oriented either intersecting or offset from the crystal axis, but transversely at a 90° angle thereto. Note too that it is axially offset from the crystal. PG y similarly has a conductor 32 coupled across it with a linear length 32' oriented transversely to the crystal axis and to the crystal itself, i.e. it is not axially offset from the crystal. PG z has a coil 34 coupled across it with three turns wrapped about the crystal. It has been found that with these three conductor configurations that PG x produces a weaker electromagnetic field about the crystal body than PG y, and that PG y produces a weaker field than PG z. Thus, the configuration of z is the preferred.

The FIG. 5 apparatus illustrates that the stimuli conductor may be linear, curved or coiled in the vicinity of the quartz crystal and still yield an effective weak electromagnetic field. It has been found that a conductor oriented parallel or near parallel with the crystal axis is ineffective. Preferably its transverse angle to the crystal axis Ag, shown 90° in FIG. 5, is at least 45°. The weak electromagnetic field produced with the angle being less than 45° does not produce noticeable stress reduction.

Though the stimuli conductor lengths 30' and 32' are shown in the drawing at non-preferred orientations, this is not meant to mean that multiple PG cannot be used. To the contrary, more than one can be used in order to generate multiple pulse trains of differing pulse widths and/or pulse repetition rates. Preferably these are in the form of three independent coils wrapped about the crystal axially spaced from each other. Alternatively, the multiple pulse trains may be generated with a single low voltage pulse generator. Indeed, with a single sweep pulse generator an entire range of frequency modulations may be employed. Alternatively, a single staircase pulse generator may be used to frequency shift through a repetition rate frequency band. Thus, with these conventional techniques a single pulse generator may be employed.

The advantage of using a single staircase pulse generator with multiple pulse trains of diverse pulse train characteristics is that more than one individual may be simultaneously treated with the apparatus with each pulse train tailored to a single individual, as previously described. In this manner, for example, a husband and wife may each be simultaneously treated with a single apparatus located in their home or vehicle. With a sweep or staircase pulse generator a large number of people may simultaneously be effectively treated. Conversely, the advantage of employing multiple pulse generators is that each generator is continually generating a weak electromagnetic field that is tailored for a particular individual. With a sweep or staircase pulse generator, the specific field generated for each individual is intermittent.

Quartz crystals with lengths of ½ to 3 inches and diameters from ⅛ inch to ½ inch have been successfully utilized. The crystals may be tinted such as amethyst, citrine or tourmaline with similar results. The pulse generator may be powered with a conventional 9-volt battery to generate pulses of 0.2 volts or more with peak currents of 1 or more microamps and with variable pulse width and pulse repetition rates. It has been found that pulse widths of between 0.1 and 50 microseconds as measured at 50% of peak voltage, and of a pulse repetition rate of between 500 Hz and 10 KHz, peak to peak, as shown in FIG. 6, produce a weak electromagnetic field about the quartz crystal that are of substantial therapeutic value in reducing physiological stress. The pulse generator power requirements are extremely low. For example, a 5 KHz pulse repetition rate, a 1 microsecond pulse width, a peak pulse voltage of 9 volts (plus or minus) and a peak conductor pulse current of 50 µamps, requires but 1.1 microwatts, rendering it ideal for battery applications. With the low voltage embodiment, the apparatus may be self contained with its power pack in a lightweight small unit of the size of an ordinary portable dictaphone or the like and thus carried on the person.

The effectiveness of the just described lower voltage applications, i.e. below 500 volts, has been proven both subjectively, from the words of the test individuals, and objectively. Objective test confirmation has been obtained with conventional finger tip temperature monitoring as conventionally used by stress reduction clinics. In conducting such tests thermal sensors were attached to the subjects' finger tips. The temperature of the finger tips was found to increase as the test continued in a constant temperature environment. Most stress reduction clinics monitor and display the adrenal gland activities of an individual as an indicator of their physiological stress level. This is accomplished by attaching thermal sensors to an individual's finger tips and monitoring their finger tip temperatures. Finger tip temperature decreases (blood withdrawal) indicates more physiological stress while a finger tip temperature increase (increased input of blood) indicates less physiological stress.

It thus is seen that a method of prescribing and treating, and apparatus for performing such, is now provided for treating physiological stress that alleviates problems associated with prior methods and apparatuses. Though the invention has been described in its preferred form, it should be understood that many modifications, additions and deletions may be made thereto without departure from the spirit and scope of the invention as set forth in the following claims.

I claim:

1. A method of treating physiological stress in a human subject which comprises the steps of:
   (a) stimulating a quartz crystal by applying electrical pulses of pulse widths between 0.1 and 50 microseconds each at a pulse repetition rate of between 0.5K and 10K pulses per second to a conductor positioned adjacent to the quartz crystal thereby generating a weak electromagnetic field, and
   (b) positioning the subject within the weak electromagnetic field.

2. The treatment method of claim 1 wherein the pulses are applied at a voltage less than 500 volts.

3. The treatment method of claim 1 wherein the pulses are applied to a conductive coil mounted about the quartz crystal.

4. The treatment method of claim 1 wherein the pulses are applied to a generally linear conductor oriented at least 45° to longitudinal axis of the quartz crystal.

5. The treatment method of claim 1 wherein the quartz crystal is stimulated by application by multiple pulse trains of diverse electrical parameters.

6. The treatment method of claim 5 wherein the multiple pulse trains are applied to the conductor.

7. The treatment method of claim 5 wherein the multiple pulse trains are applied to multiple conductors positioned adjacent to the quartz crystal.

8. The treatment method of claim 1 wherein the quartz crystal is stimulated with electrical pulses of modulated pulse repetition rates.

9. Apparatus for use in the treatment of physiological stress of a human subject which comprises, in combination, a quartz crystal, an electrical conductor mounted adjacent said quartz crystal, and means for applying to said conductor electrical pulses of pulse widths between 0.1 and 50 microseconds each at a pulse repetition rate of between 0.5K and 10K pulses per second.

10. The apparatus of claim 9 wherein said pulse application means comprises a low voltage pulse generator.

11. The apparatus of claim 10 wherein said pulse application means comprises a plurality of low voltage pulse generators.

12. The apparatus of claim 10 wherein said low voltage pulse generator comprises a battery power source.

13. The apparatus of claim 9 wherein said pulse application means comprises a frequency sweep pulse generator.

14. The apparatus of claim 9 wherein said pulse application means comprises a staircase frequency pulse generator.

15. The apparatus of claim 9 wherein said quartz crystal has a length of between ½ inch and 3 inches.

16. The apparatus of claim 9 wherein said quartz crystal has a diameter of between ⅛ inch and ½ inch.

17. The apparatus of claim 9 wherein said quarts crystal has a length of between ½ inch and 3 inches and has a diameter of between ⅛ inch and ½ inch.

* * * * *